(12) United States Patent
Greenberg et al.

(10) Patent No.: US 8,680,148 B2
(45) Date of Patent: Mar. 25, 2014

(54) METALLO-DESFERRIOXAMINE COMPLEXES AND THEIR USE IN THE TREATMENT OF BACTERIAL INFECTIONS

(75) Inventors: E. Peter Greenberg, Seattle, WA (US); Ehud Banin, Kiryat Ono (IL); Eyal Banin, Jerusalem (IL); Eduard Berenshtein, Jerusalem (IL); Mordechai Chevion, Ziyyon (IL)

(73) Assignees: University of Washington, Seattle, WA (US); Hadasit Medical Research Services and Development Ltd., Jerusalem (IL); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 1376 days.

(21) Appl. No.: 11/838,177

(22) Filed: Aug. 13, 2007

(65) Prior Publication Data

US 2008/0085866 A1 Apr. 10, 2008

Related U.S. Application Data

(60) Provisional application No. 60/837,393, filed on Aug. 11, 2006.

(51) Int. Cl.
| | | |
|---|---|---|
| *A61K 31/19* | (2006.01) | |
| *A61K 31/35* | (2006.01) | |
| *A61K 31/28* | (2006.01) | |
| *A61K 31/315* | (2006.01) | |
| *A61K 31/16* | (2006.01) | |
| *A61K 31/7008* | (2006.01) | |
| *A61K 31/65* | (2006.01) | |
| *A61K 31/43* | (2006.01) | |
| *C07C 259/06* | (2006.01) | |

(52) U.S. Cl.
CPC ............. *A61K 31/16* (2013.01); *A61K 31/7008* (2013.01); *A61K 31/65* (2013.01); *A61K 31/43* (2013.01); *C07C 259/06* (2013.01)
USPC ............ 514/575; 514/459; 514/492; 514/494

(58) Field of Classification Search
USPC .................................. 514/575, 459, 492, 494
See application file for complete search history.

(56) References Cited

U.S. PATENT DOCUMENTS

| | | | |
|---|---|---|---|
| 4,923,450 A * | 5/1990 | Maeda et al. ................. | 604/265 |
| 5,618,838 A | 4/1997 | Chevion | |
| 5,997,912 A * | 12/1999 | Schlesinger et al. .......... | 424/650 |

FOREIGN PATENT DOCUMENTS

| | | | |
|---|---|---|---|
| WO | WO 0224201 A1 * | 3/2002 | |
| WO | 2004/060490 A1 | 7/2004 | |
| WO | WO 2004056346 A1 * | 7/2004 | |

OTHER PUBLICATIONS

Banin et al. "Iron and *Pseudomonas aeruginosa* biofilm formation," PNAS, Aug. 2, 2005, vol. 102, No. 31, pp. 11076-11081.*
Banin, E., et al., Iron and *Pseudomonas aeruginosa* Biofilm Formation, Proceedings of the National Academy of Sciences (PNAS) 102(31):11076-11081, Aug. 2, 2005.

(Continued)

*Primary Examiner* — Shengjun Wang
(74) *Attorney, Agent, or Firm* — Christensen O'Connor Johnson Kindness PLLC

(57) ABSTRACT

Methods for treating a bacterial infection by using a metallo-desferrioxamine complex.

21 Claims, 13 Drawing Sheets

(56) References Cited

OTHER PUBLICATIONS

Budzikiewicz, H., "Siderophore-Antibiotic Conjugates Used as Trojan Horses Against *Pseudomonas aeruginosa*," Current Topics in Medicinal Chemistry 1(1):73-82, 2001.

Chevion, M., "Protection Against Free Radical-Induced and Transition Metal-Mediated Damage: The Use of 'Pull' and 'Push' Mechanisms," Free Radical Research Communications 12-13(Part II):691-696, Feb. 1991 (presented at the Fifth Conference on Superoxide and Superoxide Dismutase, Jerusalem, Sep. 1989).

Diarra, M.S., et al., "Species Selectivity of New Siderophore-Drug Conjugates That Use Specific Iron Uptake for Entry Into Bacteria," Antimicrobial Agents and Chemotherapy 40(11):2610-2617, Nov. 1996.

Ghosh, A., et al., "Iron Transport-Mediated Drug Delivery Using Mixed-Ligan Siderophore-β-Lactam Conjugates," Chemistry & Biology 3(12):1011-1019, Dec. 1996.

Karck, M., et al., "The Push-and-Pull Mechanism to Scavenge Redox-Active Transition Metals: A Novel Concept in Myocardial Protection," Journal of Thoracic and Cardiovascular Surgery 121(6):1169-1178, Jun. 2001.

Lowy, F.D., et al., "Susceptibilities of Bacterial and Fungal Urinary Tract Isolates to Desferrioxamine," Antimicrobial Agents and Chemotherapy 25(3):375-376, Mar. 1984.

Plaha, D.S., and H.J. Rogers, "Antibacterial Effect of the Scandium Complex of Enterochelin: Studies of the Mechanism of Action," Biochimica et Biophysica Acta 760(2):246-55, Oct. 18, 1983.

Pradines, B., et al., "In Vitro Activities of Antibiotics Against *Plasmodium falciparum* Are Inhibited by Iron," Antimicrobial Agents and Chemotherapy 45(6):1746-1750, Jun. 2001.

Robins-Browne, R.M., and J.K. Prpic, "Effects of Iron and Desferrioxamine on Infections With *Yersinia enterocolitica*," Infection and Immunity 47(3):774-779, Mar. 1985.

Rogers, H.J., et al., "Antibacterial Effect of Scandium and Indium Complexes of Enterochelin on *Klebsiella pneumoniae*," Antimicrobial Agents and Chemotherapy 18(1):63-68, Jul. 1980.

Rogers, H.J., et al., "Antibacterial Effect of the Scandium and Indium Complexes of Enterochelin on *Escherichia coli*," Journal of General Microbiology 128(10):2389-2394, Oct. 1982.

\* cited by examiner

METALLO-DESFERRIOXAMINE COMPLEXES AND THEIR USE IN THE TREATMENT OF BACTERIAL INFECTIONS

CROSS-REFERENCE TO RELATED APPLICATION

This application claims the benefit of U.S. Provisional Application No. 60/837,393, filed Aug. 11, 2006, expressly incorporated herein by reference in its entirety.

STATEMENT OF GOVERNMENT LICENSE RIGHTS

This invention was made with government support under Contract No. AI030040 awarded by the National Institute of Allergy and Infectious Diseases (NIAID). The government has certain rights in the invention.

FIELD OF THE INVENTION

The invention relates to the methods of use of desferrioxamine-metal complexes, particularly zinc and gallium complexes of desferrioxamine (DFO), in the treatment of a bacterial infection.

BACKGROUND OF THE INVENTION

Recently much attention has been focused on the need for new antimicrobial agents. Heavy antibiotic use and person-to-person spread of bacteria have greatly increased antibiotic resistant due to genetic mutation, and this problem is continually increasing in severity. The overuse of antibiotics promotes microbial resistant, which can arise from changes in microbial permeability barriers or drug-binding sites, or from the acquisition of enzymes that destroy the antimicrobial agents. The bacterium *Pseudomonas aeruginosa* is a prime example: 30% of clinical isolates from ICU or nursing home patients are now resistant to 3 or more drugs, and a similar situation exits for other organisms.

New antibacterial agents are also needed because conventional antibiotics generally work poorly in chronic infections, even when the bacteria are susceptible when tested ex vivo. A key factor accounting for this is that the infecting organisms live in biofilms, surface-associated bacterial communities encased in a polymeric matrix. An alginate film frequently surrounds the bacteria in the biofilm state. Physiological changes inherent to biofilm growth make bacteria far more resistant to killing by the immune system and antibiotics than cells in the free-living (planktonic) state. As a consequence of the biofilm lifestyle, bacteria can tolerate exposure to antibiotics and biofilm infections are notoriously difficult to treat and often impossible to cure. Examples of biofilm infections include the airway infections in cystic fibrosis (CF) patients, chronic wound, and sinus infections, endocarditis and medical devices, among other.

An approach to circumvent the resistance problem in bacterial infection is to target the transport system of the siderophores for the drug delivery into the bacterial cell. Siderophores (Greek for iron carriers) are iron chelating compounds secreted by microorganisms. The compounds are used by microorganisms to dissolve insoluble Fe(III) ions by chelation as soluble Fe(III) complexes that can be taken up by active transport mechanisms and sequestered through the cell membrane into the periplasmatic space, where the iron is set free by reduction to Fe(II). Siderophores commonly occur in two broad chemical classes, hydroxamate and catechols, one of which occurs with almost every group of bacteria. Hydroxamate siderophores includes, among other, desferrioxamine, ferrichrome, and aerobactin.

Desferrioxamine (DFO) is an iron-specific chelating agent which has been used for the treatment of iron overload since the early 1960s. The antibacterial and antifungal activity of desferrioxamine was evaluated and reported to have limited potential as an antibacterial agent. Lowy, F. D. et al., *Antimicrobial Agents and Chemotherapy* 25(3):375-376, 1984. In previous studies, it has been shown that systemic treatment with zinc-desferrioxamine (DFO-Zn) and gallium-desferrioxamine (DFO-Ga) reduced damage to the retina subjected to ischemia and reperfusion, in accord with their enhanced infiltrability through the blood-retinal barrier. See Ophir, A. et al., *Invest. Opthalmol. Vis. Sci.* 35:1212-22, 1994; and Banin, E. et al., *Free Radic. Biol. Med.* 28:315-23, 2000. Likewise, topical application of DFO-Zn reduced corneal damage following alkali burn. See Siganos, C. et al., *Cornea* 17:191-50, 1998. In addition, it has been reported that the gallium-desferrioxamine is useful in the treatment of free radical-induced pathological conditions; the treatment of injury resulting from ischemic insult to the heart, brain, or kidney; the treatment of thalassemia; the treatment of hemochromatosis; the treatment of Wilson's disease; the treatment of paraguate toxicity; or for exchanging gallium for iron. See U.S. Pat. No. 5,618,838 issued to Chevion et al. Several siderophore-antibiotic conjugates have been developed to be used as antibacterial agents. Budzikiewicz, H. *Current Topics in Medicinal Chemistry* 1:73-83, 2001. However, these conjugates have not produced promising results in controlling or eradicating biofilm formation.

Therefore, there is a need for an antibacterial agent that is effective against drug resistant bacterial infection and biofilm-forming bacteria. The present invention seeks to fulfill these needs and provides further related advantages.

SUMMARY OF THE INVENTION

The present invention provides methods for treating bacterial infection and inhibiting bacterial growth.

In one aspect, the present invention provides a method for treating human or animal subject in need of such treatment, comprising administering to the subject an amount of a metallo-desferrioxamine complex effective to inhibit bacterial infection in the subject, wherein the metallo-desferrioxamine complex comprises a metal ion selected from the group consisting of gallium and zinc.

In one embodiment, the metallo-desferrioxamine complex is gallium-desferrioxamine. In another embodiment, the metallo-desferrioxamine complex is zinc-desferrioxamine.

Representative bacterial infection that can be treated with the methods of the presenting invention includes an infection of a bacteria selected from the group consisting of *Staphylococcus aureus, Staphylococcus epidermidis, Escherichia coli, Klebsiella pneumoniae, Proteus mirabilis, Alcaligenes faecalis*, and *Neisseria meningitidis*, and species of *Salmonella, Enterobacter, Pseudomonas*, and *Providencia*. In one embodiment, the bacterial infection is a *Pseudomonas aeruginosa* infection.

The bacterial infection can be an infection of the eyes, lungs, gut, or oral cavity. In one embodiment, the bacterial infection is an acute ulcerative corneal infection. In another embodiment, the bacterial infection is a chronic biofilm-associated lung infection.

The metallo-desferrioxamine complex of the present invention can be administered in combination with an antibacterial agent.

The antibacterial agent that is useful for the present invention can be an agent selected from a group consisting of aminoglycosides, penicillins, cephalosporins, macrolides, fluoroquinolones; sulfonamides, tetracyclines, and doxycyclines. Representative antibacterial agents include gentamicin, tobramycin, amoxicillin, cephalexin, erythromycin, clarithromycin, azithromycin, ciprofloxacin, levofloxacin, ofloxacin, co-trimoxazole, trimethoprim, sumycin, panmycin, and vibramycin.

In one embodiment, the metallo-desferrioxamine complex is gallium-desferrioxamine and the antibacterial agent is gentamicin.

In another aspect, the present invention provides a method of inhibiting bacterial growth comprising contacting bacteria with an amount of a metallo-desferrioxamine complex effective to inhibit growth of the bacteria.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3 compares 3D-reconstructed confocal microscope images of six-day old biofilms of *Pseudomonas aeruginosa* cells expressing GFP.

FIG. 4 shows the survival of *P. aeruginosa* in a six-day old biofilms stained with propidium iodide in the absence of any antibacterial agent.

FIG. 5 shows the survival of *P. aeruginosa* in a six-day old biofilms treated with Gm (50 μg/mL) for 24 h and stained with propidium iodide.

FIG. 6 shows the survival of *P. aeruginosa* in a six-day old biofilms treated with DFO (1 mM) for 24 h and stained with propidium iodide.

FIG. 7 shows the survival of *P. aeruginosa* in a six-day old biofilms treated with Ga (1 mM) for 24 h and stained with propidium iodide.

FIG. 8 shows the survival of *P. aeruginosa* in a six-day old biofilms treated with DFO-Ga (1 mM) for 24 h and stained with propidium iodide.

FIG. 13 shows representative images of a normal uninfected rabbit cornea.

FIG. 14 shows representative images of a rabbit cornea infected with *P. aeruginosa* after treating with artificial tears, a sham treatment, for 96 h.

FIG. 15 shows representative images of a rabbit cornea infected with *P. aeruginosa* after treatment with gentamicin for 96 h.

FIG. 16 shows representative images of a rabbit cornea infected with *P. aeruginosa* after treatment with the combination of desferrioxamine and gentamicin for 96 h.

FIG. 17 shows representative images of a rabbit cornea infected with *P. aeruginosa* after treatment with the combination of gallium and gentamicin for 96 h.

FIG. 18 shows representative images of a rabbit cornea infected with *P. aeruginosa* after treatment with the combination of gallium-desferrioxamine and gentamicin for 96 h.

DETAILED DESCRIPTION OF THE INVENTION

Figure 1:
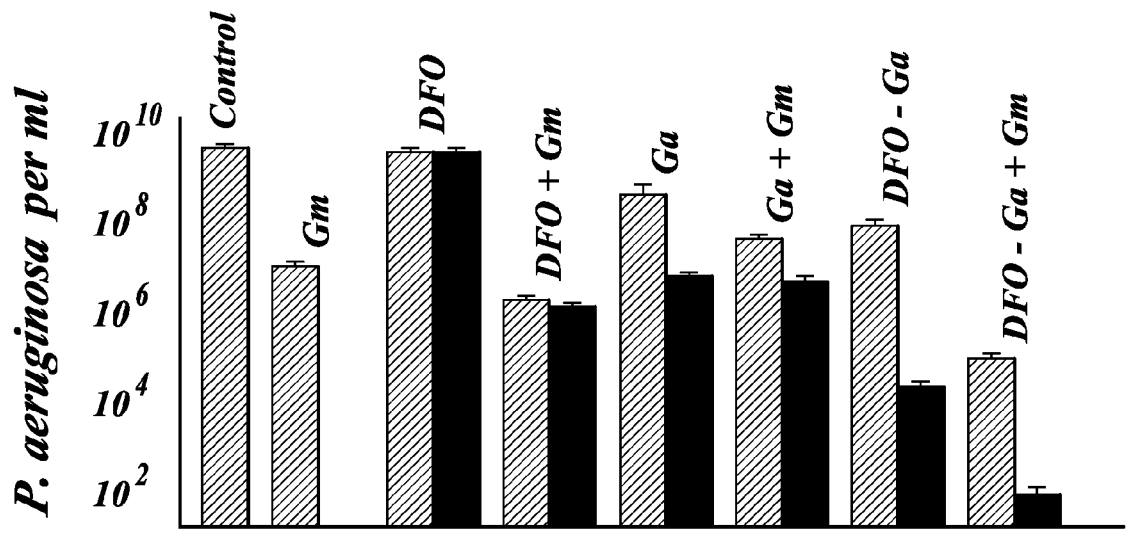
FIG. 1 is a bar graph illustrating the survival of stationary phase *Pseudomonas aeruginosa* cells treated for 24 hours with desferrioxamine (DFO), gentamicin (Gm), gallium (Ga), gallium-desferrioxamine (DFO-Ga), DFO and Gm, Ga and Gm, and DFO-Ga and Gm. The concentrations used for each compound were 0.1 mM (shaded) or 1 mM (dark) for DFO, Ga or DFO-Ga and 10 μg/mL for Gm.

In one aspect, the present invention provides a method for treating human or animal subject in need of such treatment, comprising administering to the subject an amount of a metallo-desferrioxamine complex effective to inhibit bacterial infection in the subject, wherein the metallo-desferrioxamine complex comprises a metal ion selected from the group consisting of gallium and zinc.

In another aspect, the present invention provide methods for inhibiting bacterial growth.

In one embodiment, the method includes the step of contacting bacteria with an amount of a metallo-desferrioxamine complex effective to inhibit growth of the bacteria. In another embodiment, the method includes the step of administering an effective amount of a metallo-desferrioxamine complex to a host having bacterial infection. In another embodiment, the method includes the step of contacting bacteria in a biofilm state with an amount of metallo-desferrioxamine complex effective to inhibit formation of the biofilm.

The metallo-desferrioxamine complex of the invention can be used to prevent the growth of bacteria (for prophylactic purposes), inhibit the growth of bacteria and/or kill bacteria, and prevent or inhibit biofilm formation. In addition, the metallo-desferrioxamine complex can be used to prevent, or decrease bacterial growth on medical devices, including implants and stents. The devices may be rinsed with a solution containing the compounds of the invention, or may be coated with formulation carriers holding the compounds of the invention and enabling their slow release.

The metallo-desferrioxamine complex may be made as described in PCT application publication number WO 04060490, which is hereby incorporated by reference.

Desferrioxamine is a siderphore chelating agent. Desferrioxamine forms complexes predominantly with ferric iron and with trivalent aluminium ions: the complex formation constants are $10^{31}$ and $10^{25}$, respectively. The affinity of desferrioxamine for divalent ions, such as $Fe^{2+}$, $Cu^{2+}$, $Zn^{2+}$, $Ca^{2+}$, is substantially lower (complex formation constants $10^{14}$ or below). Chelation occurs at a 1:1 molar basis, so that 1 g desferrioxamine can theoretically bind 85 mg ferric iron or 41 mg aluminum ion.

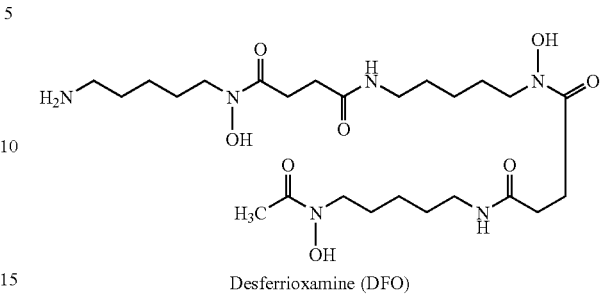

Desferrioxamine (DFO)

In one embodiment, the metallo-desferrioxamine complex is a gallium-desferrioxamine complex. In another embodiment, the metallo-desferrioxamine complex is a zinc-desferrioxamine complex.

Gallium (Ga) has an ionic radium nearly identical to that of Fe, and many biological systems are unable to distinguish Ga(III) from Fe(III). Ga can disrupt Fe-dependent processes because, unlike Fe(III), Ga(III) cannot be reduced, and sequential oxidation and reduction are critical for many of Fe's biological functions.

Zinc-desferrioxamine (DFO-Zn) and gallium-desferrioxamine (DFO-Ga) are known metal complexes, which inhibit the catalysis of iron and copper in the formation of the free radicals. Their protective activity can be visualized through the "pulling" out of redox active iron that is responsible for the production of the hydroxyl radicals via chelation by the DFO component. At the same time, the relatively inert zinc (or gallium) iron, that is liberated during the exchange or iron within the complex, further acts as a secondary antioxidant, by "pushing" out an additional iron ion from its binding site. See Chevion, M., *Free Radic. Biol. Med.* 5:27-37, 1988; and Chevion, M., *Free Radic. Res. Commun.* 12-13:691-6, 1991. The spatial structure of these complexes is markedly different from that of DFO alone, allowing their enhanced infiltrability into cells and tissues. See Chevion et al. (1991) id ibid.

The metallo-desferrioxamine complexes of the invention are useful in vitro or in vivo in treating a bacterial infection. The metallo-desferrioxamine complexes may be used alone or in compositions together with a pharmaceutically acceptable carrier or excipient. The administration may be formulated as a slow or sustained release delivery system.

Pharmaceutical compositions of the present invention comprise a therapeutically effective amount of a metallo-desferrioxamine complex described herein formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Other suitable pharmaceutically acceptable excipients are described in "Remington's Pharmaceutical Sciences," Mack Pub. Co., New Jersey, 1991, incorporated herein by reference.

The metallo-desferrioxamine complex of the invention may be administered to a subject suffering from a bacterial infection in any manner used in the art including ophthalmically (for example, included in a solution for contact lenses), orally, parenterally, sublingually, by aerosolization or inhalation spray, rectally, intracisternally, intravaginally, intraperitoneally, bucally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Methods of formulation are well known in the art and are disclosed, for example, in Remington: *The Science and Practice of Pharmacy*, Mack Publishing Company, Easton, Pa., 19th Edition (1995). Pharmaceutical compositions for use in the present invention can be in the form of sterile, non-pyrogenic liquid solutions or suspensions, coated capsules, suppositories, lyophilized powders, transdermal patches or other forms known in the art.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-propanediol or 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations may also be prepared by entrapping the drug in liposomes or microemulsions, which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active metallo-desferrioxamine complexes of the present invention can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of a metallo-desferrioxamine complex of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles.

Aerosolized formulations of the invention may be delivered using an aerosol forming device, such as a jet, vibrating porous plate or ultrasonic nebulizer, preferably selected to allow the formation of an aerosol particles having with a mass median aerodynamic diameter predominantly between 1 to 5 µm. Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Metallo-desferrioxamine complexes of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq.

For pharmaceutical applications, effective amounts of the metallo-desferrioxamine complexes of the invention generally include any amount sufficient to inhibit growth of bacteria in a subject suffering from a bacterial infection. The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

According to the methods of treatment of the present invention, a bacterial infection is reduced or eliminated in a patient such as a human or lower mammal by administering to the patient a therapeutically effective amount of a metallo-desferrioxamine complex of the invention, in such amounts and for such time as is necessary to achieve the desired result. By a "therapeutically effective amount" of a compound of the invention is meant a sufficient amount of the compound to treat bacterial growth, at a reasonable benefit/risk ratio applicable to any medical treatment. It will be understood, however, that the total daily usage of the complexes and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose. In general, treatment regimens according to the present invention comprise administration to a patient in need of such treatment from about 10 mg to about 2000 mg of the compound(s) of this invention per day in single or multiple doses.

The metallo-desferrioxamine complex of the present invention can be administered in combination with an additional antibacterial agent.

Suitable additional antibacterial agent can be any agent with bacterial inhibition activity. Representative additional antibacterial agent includes, for example, compounds selected from a group consisting of aminoglycosides such as gentamicin (GARAMYCIN™) and tobramycin (TOBREX™); penicillins such as amoxicillin; cephalosporins such as cephalexin (KEFLEX™); macrolides such as erythromycin (E-MYCIN™), clarithromycin (BIAXIN™) and azithromycin (ZITHROMAX™); fluoroquinolones such as ciprofloxacin (CIPRO™), levofloxacin (LEVAQUIN™) and ofloxacin (FLOXIN™); sulfonamide such as co-trimoxazole (BACTRIM™) and trimethoprim (PROLOPRIM™); tetracyclines such as sumycin and panmycin; and doxycycline such as vibramycin.

In one embodiment, the additional antibacterial agent is an antibiotic of the family of cephalosporin or quinolone, which may be used for example, in opthalmology. In one embodiment, the antibacterial agent is gentamicin.

The method of the invention may be used to treat infection of any bacteria that has a desferrioxamine uptake system, including bacteria that exist in the free-living and/or biofilm state.

The bacterial infection can be an infection of a bacterial from a family of *Salmonella, Enterobacter, Pseudomonas*, and *Providencia*. The representative bacterium include *Staphylococcus aureus, Staphylococcus epidermidis, Escherichia coli, Klebsiella pneumoniae, Proteus mirabilis, Alcaligenes faecalis*, and *Neisseria meningitidis*. In one embodiment, the bacteria is *Pseudomonas aeruginosa*.

For example, the methods of the present invention may be used to treat any *Pseudomonas aeruginosa* infection in a mammalian subject, such as an acute ulcerative corneal infection or chronic biofilm-associated lung infection in cystic fibrosis patients. The methods of the invention may also be used to treat bacteria present in the eyes, lungs, gut, or oral cavity, or bacteria that tend to develop on medical devices such as stents and implants.

In one embodiment, the bacterial infection that can be treated by the methods of the present invention is a chronic biofilm-associated lung infection.

*Pseudomonas aeruginosa* biofilm infections are a major medical concern. For example, this bacterium causes chronic biofilm-associated lung infections in cystic fibrosis patients, and acute ulcerative corneal infections, particularly in contact-lens users. The present invention provides a method of treating *Pseudomonas aeruginosa* with a metallo-complex comprising gallium-desferrioxamine or zinc-desferrioxamine.

*Pseudomonas aeruginosa* has two uptake systems for desferrioxamine-Fe. Desferrioxamine-Fe is chemically and structurally similar to gallium-desferrioxamine. Gallium interferes with iron metabolism and is toxic to bacterial cells by virtue of it's ability to compete with iron at iron binding sites of proteins. Gallium-desferrioxamine could interfere with iron homeostasis in *Pseudomonas aeruginosa*, and can serve as a carrier that delivers toxic gallium to *Pseudomonas aeruginosa* cells where it can exert its toxicity. The fact that there are two desferrioxamine transport systems makes evolution of resistance considerably more difficult than evolution of resistance in a single step.

The effect of gallium-desferrioxamine on planktonic *Pseudomonas aeruginosa* was first examined in a low iron medium. The minimal inhibitory concentration (MIC) was 32 µM. A similar result was obtained for gallium alone. Desferrioxamine did not inhibit growth, even at a concentration of 1 mM. When in the stationary phase, *Pseudomonas aeruginosa* is not effectively killed by antibiotics.

Part of the explanation for biofilm resistance to antibiotic treatment is that a large fraction of the bacterial cells in a biofilm are likely to be in a stationary phase-like state. To determine whether this was the case with gallium-desferrioxamine, the ability of this agent to kill stationary phase cells was tested and compared with a antibiotics, gentamycin.

The effect of gallium-desferrioxamine on planktonic *Pseudomonas aeruginosa* was examined in Example 1. The result shown in FIG. 1 indicates that gallium-desferrioxamine causes 10-100 times more killing of the bacteria than gentamicin.

The effect of gallium-desferrioxamine on *Pseudomonas aeruginosa* biofilm was examined in Example 2. The in vitro experiments indicate that gallium-desferrioxamine is an affective antimicrobial that can kill *Pseudomonas aeruginosa* cells growing in biofilms under a variety of conditions. The experimental results were shown in FIGS. 2-9. The experiments also show that gallium-desferrioxamine and gentamicin when used together are particularly effective in killing biofilm bacteria.

In order to confirm that the sensitivities observed with the laboratory strain of *Pseudomonas aeruginosa* (PAO1) would hold with other clinical isolates of the bacterium, the effects of gallium-desferrioxamine on 15 clinical isolates of the same bacterium were examined in Example 3. The result shown in FIG. 10 indicates that all of the strains had increased sensitivity to gallium-desferrioxamine and the combination of gallium-desferrioxamine and gentamicin treatments compared to the gentamicin treatment alone.

In one embodiment, the bacterial infection that can be treated by the method of the present invention is an acute ulcerative corneal infection.

Ulcerative keratitis is a rapidly progressive inflammatory response to a bacterial infection of the cornea. Due to its potential to permanently impair vision or even cause blindness, bacterial keratitis is an opthalmologic emergency necessitating rapid initiation of topical antibiotics at high concentrations with frequent dosing. Increased use of soft contact lenses has led to a dramatic rise in the occurrence of bacterial keratitis, particularly due to *Pseudomonas aeruginosa* infections. Because the eye is accessible and the infection can be treated aggressively by washing with high concentrations of topical antibiotic it is often possible to cure these biofilm infections and prevent the devastating complication of endophthalmitis. However, scarring and loss of corneal clarity are frequent sequel, which may lead to visual impairment. Thus, a secondary aim of treatment is to limit the residual area of corneal scarring and opacity to a minimum.

An experimental rabbit cornea infection that closely resembles keratitis caused by *Pseudomonas aeruginosa* in humans was used to examine the efficacy of gallium-desferrioxamine as an anti-Pseudomonas agent during an animal infection. As shown in Example 6, a dosing regimen similar to that used for human infections was chosen in the rabbit model of *Pseudomonas aeruginosa* infection. The results shown in FIGS. 13-20 indicate that addition of gallium-desferrioxamine to the gentamicin treatment results in a less aggressive infection and allows for faster healing. Additional parameters of disease severity such as corneal opacity, iris injection, and degree of hypopion are also improved following addition of topical gallium-desferrioxamine to the gentamicin treatment.

EXAMPLES

Bacterial strains and culture conditions. *Pseudomonas aeruginosa* PAO1 or PAO1 derivatives were used for all experiments except where noted. For flow cell biofilm experiments, strains containing the GFP expression vector pMRP9-1 were used. Both flow cell and disc reactor biofilms were grown in 1% Tryptic Soy Broth (TSB) (Becton Dickinson, Sparks, Md.) as were planktonic cultures. All cultures were incubated at 37° C. unless otherwise indicated. For the static biofilm formation assay we used M63 minimal medium supplemented with glucose (0.2%), arginine (0.4%) and $MgSO_4$ (1 mM).

Example 1

Effects of Gallium-desferrioxamine on Planktonic *Pseudomonas aeruginosa*

The minimal inhibitory concentrations (MICs) of various agents were determined by using 96-well plates. Each well contained 100 µl of 1% TSB plus test compound. The inoculum was $5 \times 10^5$ *Pseudomonas aeruginosa* cells per well. To test the effect of agents on survival of stationary phase cells, cultures inoculated with $10^5$ cells per ml and incubated for 18 h at 37° C. with aeration were used. The 18-h cultures were centrifuged. The pelleted cells were washed twice and suspended in a volume of fresh medium equal to the original culture volume. The cells were incubated at 37° C. for an additional 2 h with shaking and then exposed to the test compounds at the indicated concentrations for 24 h. Viability was determined by plating dilutions on LB agar.

FIG. 1 illustrates the survival of stationary phase *Pseudomonas aeruginosa* cells treated for 24 hours with desferrioxamine (DFO), gentamicin (Gm), gallium (Ga), gallium-desferrioxamine (DFO-Ga), DFO and Gm, Ga and Gm, and DFO-Ga and Gm. The concentrations used for each compound were 0.1 mM (shaded) or 1 mM (dark) for DFO, Ga or DFO-Ga and 10 mL for Gm. As shown in FIG. 1, after a long incubation period, gentamicin (10 µg per ml, >10 times the MIC) reduces viability by three log units, while gallium-desferrioxamine (1 mM) causes 10-100 times more killing. Because gallium-desferrioxamine and gentamicin exert their antimicrobial effects via different mechanisms, the two agents were combined and the combined treatment results in a six-log reduction in viable cells.

Example 2

Effects of Gallium-desferrioxamine on *Pseudomonas aeruginosa* Biofilm

*Pseudomonas aeruginosa* biofilms were studied in three different ways. To evaluate gallium-desferrioxamine as a biofilm-blocking agent, the biofilm formation under static growth conditions was measured in microtiter dish wells. Biofilms were grown under static conditions in 96-well microtiter dishes for 18 h at 37° C. in M63 medium with or without added agents as indicated. Attached biomass was stained with crystal violet and the degree of crystal violet staining was measured.

Figure 2:
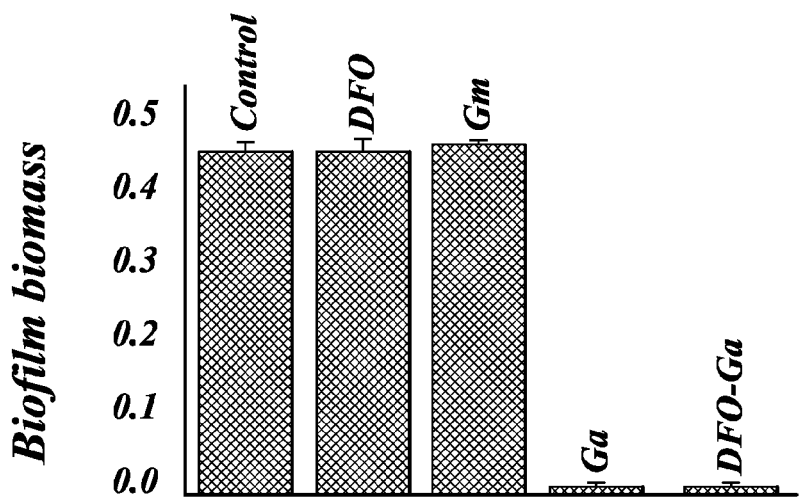
FIG. 2 is a bar graph illustrating biofilm growth of *Pseudomonas aeruginosa* cells in polyvinylchloride microtiter dish wells after treatment for 18 hours with desferrioxamine, Ga, gentamicin, or desferrioxamine-Ga. The concentrations used for each compound were 1 μM for DFO, Ga and DFO-Ga, and 0.1 μg/mL for Gm. Attached biofilm biomass was determined by measuring crystal violet binding.
Figure 3A:
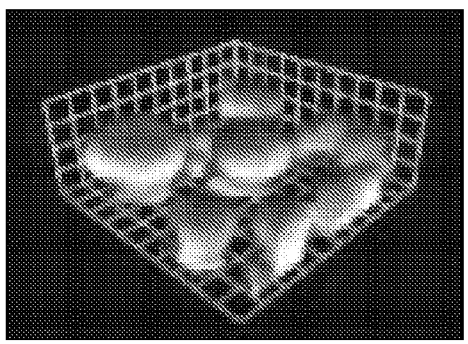
FIG. 3A shows the images of the biofilms in the absence of any antibacterial agent.
Figure 3B:
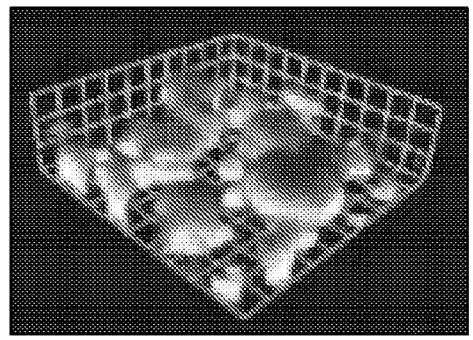
FIG. 3B shows the image of the biofilms treated for 24 hours with gentamicin (0.1 μg/mL)
Figure 3C:
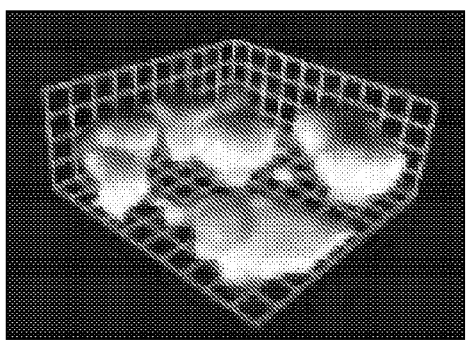
FIG. 3C shows the image of the biofilms treated for 24 hours with desferrioxamine (1 μM)
Figure 3D:
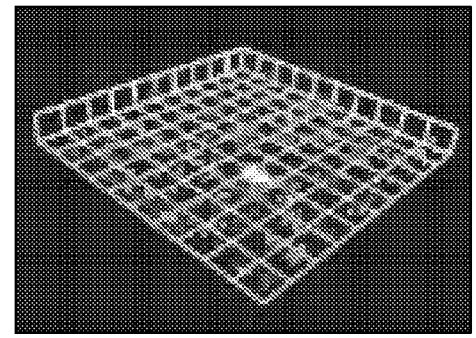
FIG. 3D shows the image of the biofilms treated for 24 hours with Ga (1 μM)
Figure 3E:
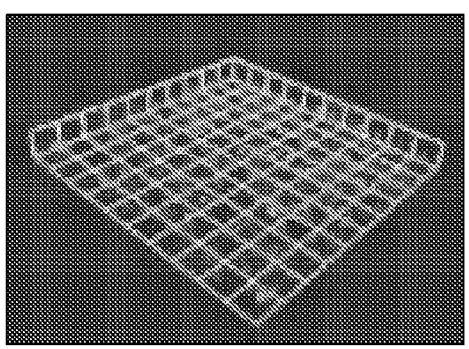
FIG. 3E shows the image of the biofilms treated for 24 hours with gallium-desferrioxamine (1 μM).

FIG. 2 illustrates the biofilm growth of *Pseudomonas aeruginosa* cells in polyvinylchloride microtiter dish wells after treatment for 18 hours with desferrioxamine, Ga, gentamicin, or desferrioxamine-Ga. The concentrations used for each compound were 1 µM for DFO, Ga and DFO-Ga, and 0.1 µg/mL for Gm. Attached biofilm biomass was determined by measuring crystal violet binding. FIG. 2 shows that addition of desferrioxamine (1 µM) or sub-inhibitory concentrations of gentamicin (0.1 µg per ml) does not affect biofilm formation. When sub-inhibitory concentrations of gallium-desferrioxamine (1 µM) or gallium alone (1 µM) are used, biofilm formation is effectively blocked.

The development of biofilms under a continuous flow of medium was followed in microscope observation chambers. To visualize biofilms grown under a continuous flow of medium, flow cells and confocal microscopy with an incubation temperature of 25° C. were used. An agent was added to the medium at the beginning of an experiment to determine whether the agent prevented biofilm formation. To determine the affect of an agent on mature biofilms, the biofilm was allowed to grow for six days prior to addition of the test compound. To discriminate live and dead cells, propidium iodide (PI, 30 µM, Sigma Chemical Co., St. Louis, Mo.) was used.

FIG. 3 compares 3D-reconstructed confocal microscope images of six-day old biofilms of *Pseudomonas aeruginosa* cells expressing GFP treated for 24 hours with gentamicin (0.1 µg/mL), desferrioxamine (1 µM), gallium (1 µM), and gallium-desferrioxamine (1 µM). Under these experimental conditions, *Pseudomonas aeruginosa* develops mushroom-like structures containing cells embedded in a self-produced matrix (FIGS. 3A-3E). FIG. 3E shows that the presence of gallium-desferrioxamine (1 µM) completely blocks biofilm formation.

Figure 4A:
FIG. 4A is a saggital reconstruction image.
Figure 5A:
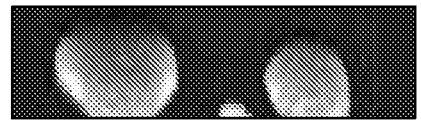
FIG. 5A is a saggital reconstruction image.
Figure 4B:
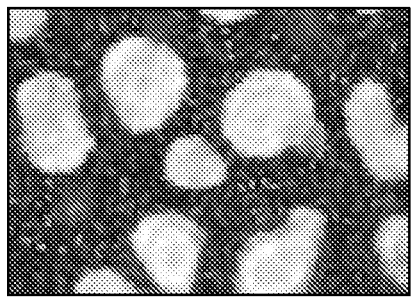
FIG. 4B is the image of horizontal section.
Figure 5B:
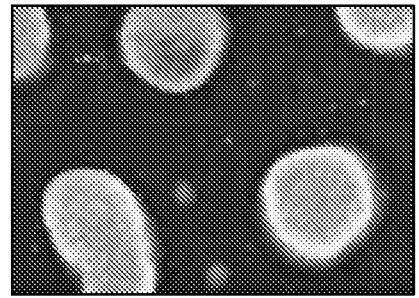
FIG. 5B is the image of horizontal section.
Figure 4C:
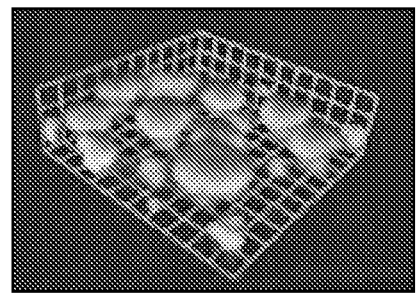
FIG. 4C is a 3-D reconstruction image.
Figure 5C:
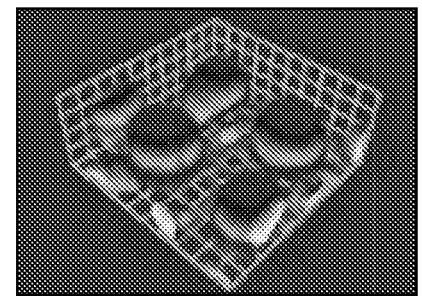
FIG. 5C is a 3-D reconstruction image.
Figure 6A:
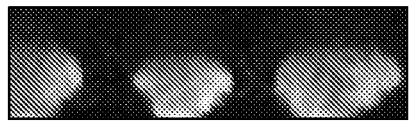
FIG. 6A is a saggital reconstruction image.
Figure 7A:
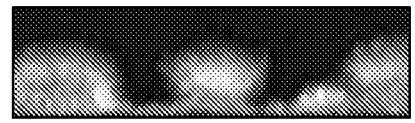
FIG. 7A is a saggital reconstruction image.
Figure 6B:
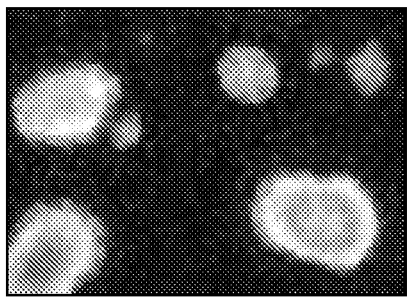
FIG. 6B is the image of horizontal section.
Figure 7B:
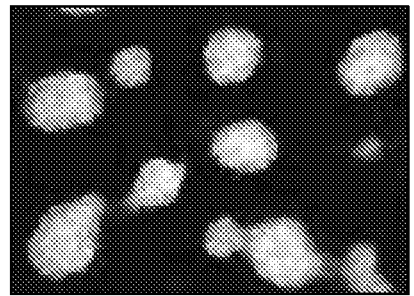
FIG. 7B is the image of horizontal section.
Figure 6C:
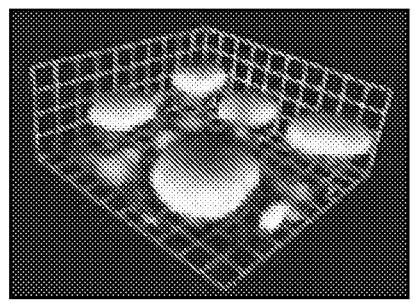
FIG. 6C is a 3-D reconstruction image.
Figure 7C:
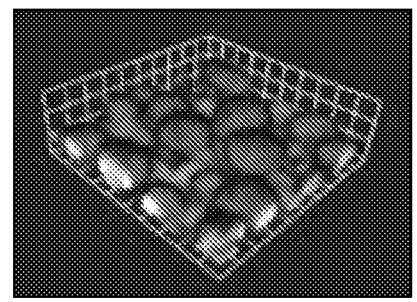
FIG. 7C is a 3-D reconstruction image.
Figure 8A:
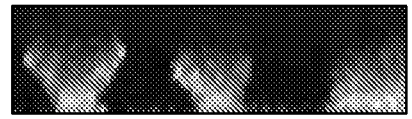
FIG. 8A is a saggital reconstruction image.
Figure 8B:
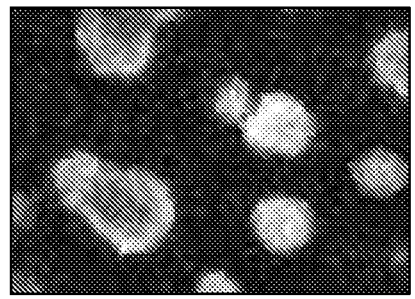
FIG. 8B is the horizontal section image.
Figure 8C:
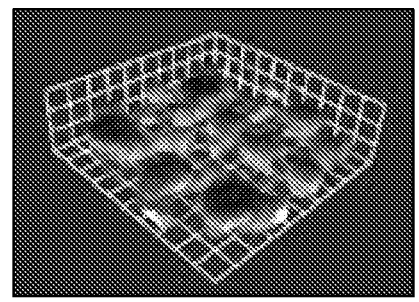
FIG. 8C is a 3-D reconstruction image.

FIGS. 4-8 compare the survival of *P. aeruginosa* in a six-day old biofilms stained with propidium iodide under with different treatment. FIG. 4 shows the survival of *P. aeruginosa* in the absence of any antibacterial agent. FIG. 5 and FIG. 7 show that addition of gentamicin (50 µg/ml) or gallium (1 mM) causes killing of cells in the outer regions of the biofilm only as detected by an increase in red propidium iodide staining in these areas. FIG. 6 shows that desferrioxamine does not appear to kill cells in mushroom-like structures. FIG. 8 shows that, after treatment with gallium-desferrioxamine (1 mM) for 24 h, gallium-desferrioxamine causes death of cells throughout the mushroom-like structures in the biofilm.

A spinning disc reactor as a third method was used to study biofilms. The biofilms grown under different conditions were tested and the activity of gallium-desferrioxamine against biofilms grown in a spinning disc reactor under continuous flow with high shear was examined. In this system biofilms are grown under a flow of medium and at high shear forces. After 24 h in a flow of medium, the polycarbonate chips with attached biofilm bacteria were removed from the spinning disc and washed 3 times in PBS. All incubations for spinning disc experiments were at 37° C. These biofilms were then exposed to the indicated agents in water for 24 h. Cells that detached from the biofilm during the treatment were enumerated by plating on LB agar. To estimate the number of remaining attached biofilm cells, the discs were placed in 1 ml PBS and the cells were dispersed by using a tissue homogenizer (Brinkman Homogenizer, Westbury, N.Y.). Viable cell numbers were determined by plating on LB agar.

Figure 9:
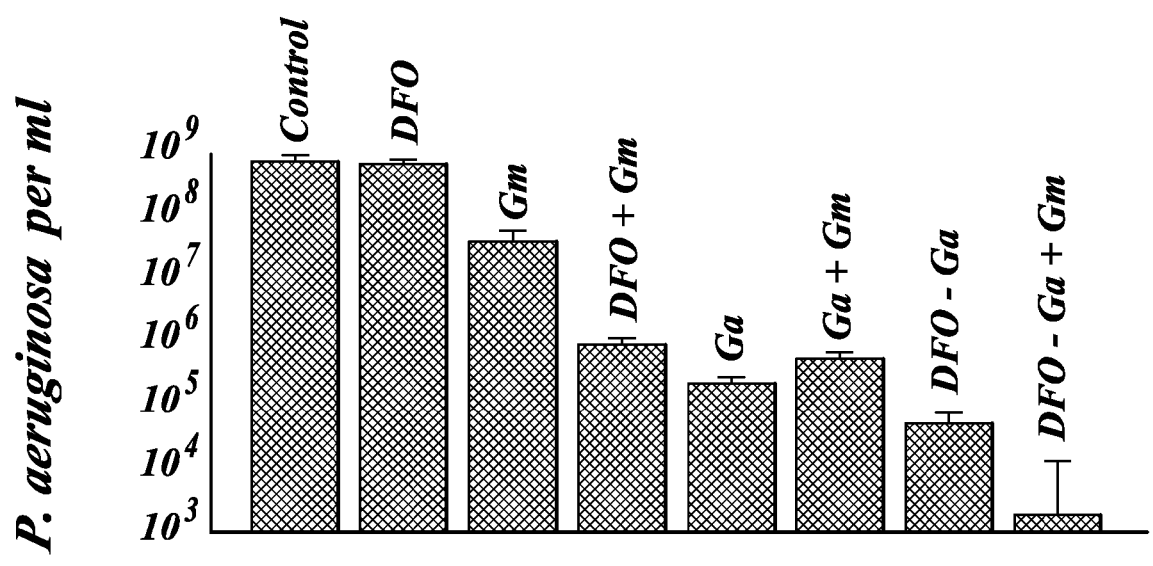
FIG. 9 is a bar graph illustrating the results from the treatment of spinning disc reactor biofilms of *P. aeruginosa* cells after treatment for 24 hours with desferrioxamine (1 mM), gentamicin (50 μg/mL), gallium (1 mM), gallium-desferrioxamine (1 mM), the combination of desferrioxamine (1 mM) and Gm (50 μg/mL), the combination of gallium (1 mM) and gentamicin (50 μg/mL), and the combination of gallium-desferrioxamine (1 mM) and gentamicin (10 μg/mL)

As shown in FIG. 9, spinning disc biofilms treated with gentamicin (50 µg/mL) showed a 2-log decrease in cell counts. gallium-desferrioxamine (1 mM) caused a 3-4-log decrease in cell counts. Furthermore, when gallium-desferrioxamine and gentamicin are used together, viability is reduced by almost 6 logs, leaving only a few viable cells.

The in vitro experiments described above indicate that gallium-desferrioxamine is an effective antimicrobial that can kill *Pseudomonas aeruginosa* cells growing planktonically, it can kill cells in stationary phase as well as cells growing in biofilms under a variety of conditions. The experiments also show that gallium-desferrioxamine and gentamicin when used together are particularly effective in killing biofilm bacteria.

Example 3

Effects of Gallium-Desferrioxamine on *Pseudomonas aeruginosa* Clinical Isolates Biofilms To verify that the sensitivities observed with laboratory strain of *P. aeruginosa* (PAO1) would hold with other clinical isolates of the bacterium, 15 clinical isolates of the same bacterium obtained from CF, eye and wound infected patients were screened. The group of isolates tested included mucoid strains, and strains with a variety of drug resistance profiles. The spinning-disc biofilm reactor system was utilized. In this system biofilms are grown under a flow of medium and at high shear forces. After 24 h in a flow of medium the polycarbonate chips with attached biofilm bacteria were removed from the spinning disc and washed 3 times in PBS. All incubations for spinning disc experiments were at 37° C. These biofilms were then exposed to Gm (50 µg/ml), DFO-Ga (1 mM) or a combination of gallium-desferrioxamine (10 µg/mL) and gentamicin (1 mM) in water for 24 h. To estimate the number of remaining attached biofilm cells, we placed the discs in 1 ml PBS and dispersed the cells by using a tissue homogenizer (Brinkman Homogenizer, Westbury, N.Y.). Viable cell numbers were determined by plating on LB agar.

Figure 10:
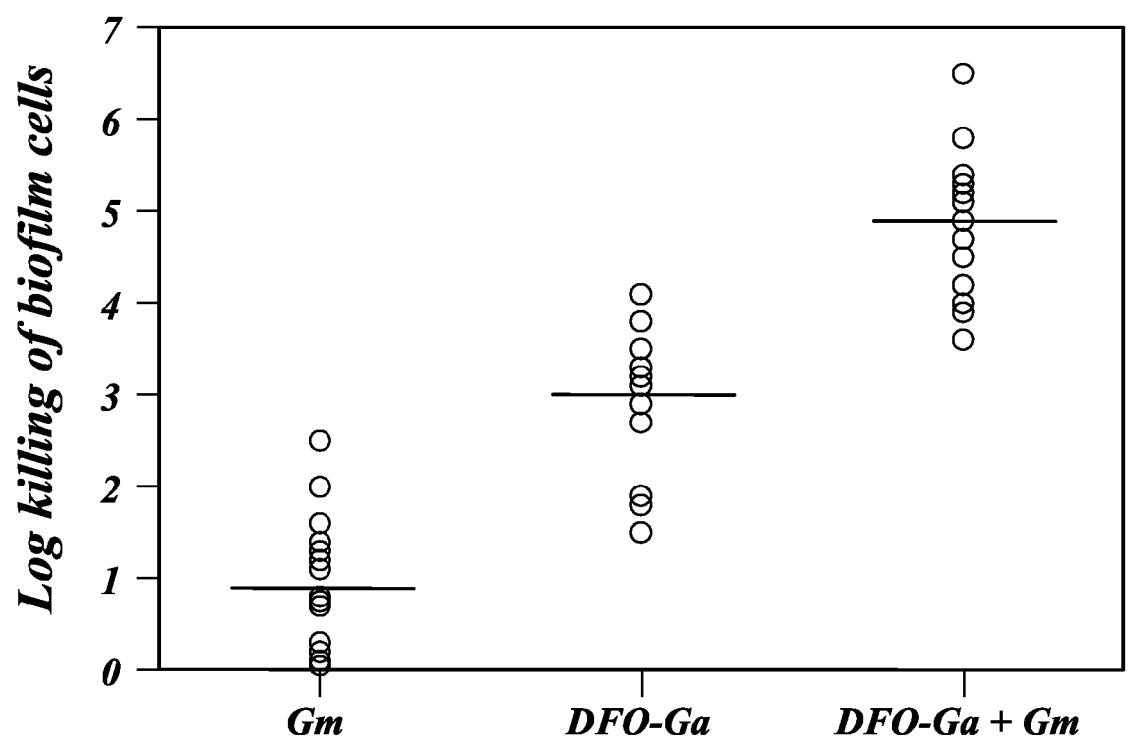
FIG. 10 compares the sensitivity of *P. aeruginosa* clinical biofilm cells to Gm, DFO-Ga, and the combination of gentamicin and gallium-desferrioxamine.

All of the strains including the drug resistant ones had increased sensitivity to gallium-desferrioxamine (3.02 log killing) and the combination of gallium-desferrioxamine and gentamicin (4.92 log killing) treatments compared to the gentamicin treatment alone (only 0.95 log killing) (FIG. 10). This suggests that gallium-desferrioxamine is effective in treating *P. aeruginosa* infections.

Example 4

Effects of Gallium-Desferrioxamine on Iron Regulation in *Pseudomonas aeruginosa* Cell To study the effect of DFO-Ga on iron regulation in the cell, a *P. aeruginosa* PAO1 strain-carrying GFP fused to an iron starvation promoter (pvdA-GFP) was constructed. The promoter is induced under iron limitation. Free living PAO1 carrying pvdA-GFP fusion, i.e., an iron starvation reporter fusion, $10^9$ cell/ml in 1% TSB were exposed to 100 micromolar of Ga (1 mM), DFO (1 mM), or DFO-Ga (1 mM) for 1 h at 37° C.

Figure 11:
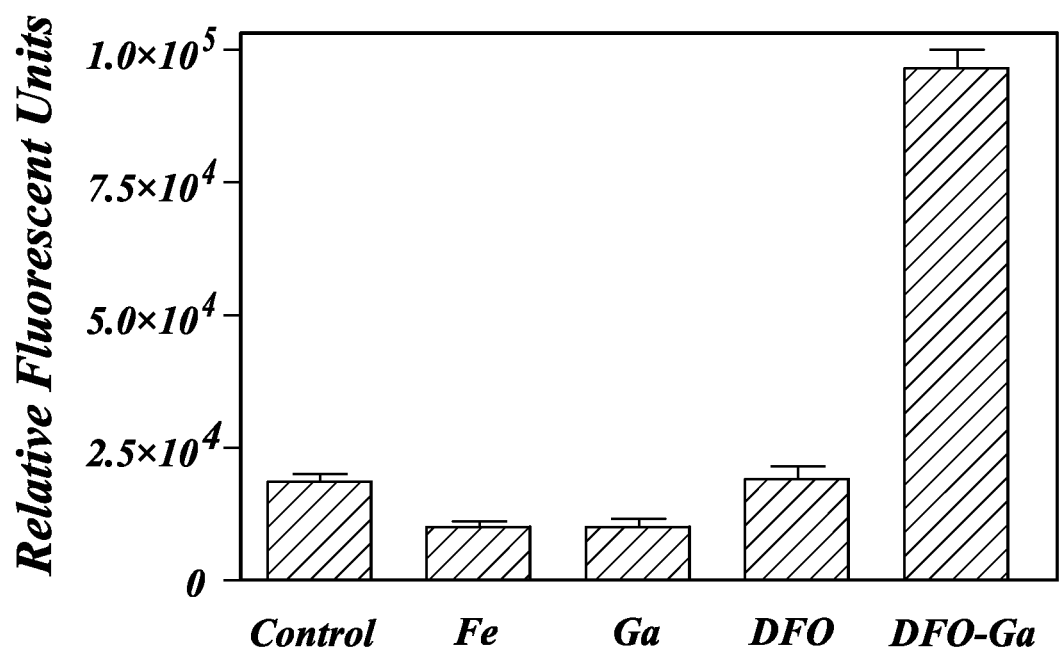
FIG. 11 shows the iron starvation response in *P. aeruginosa* induced by the exposure to gallium-desferrioxamine.

As shown in FIG. 11, exposure to gallium-desferrioxamine (1 mM) caused a four-fold induction in relative fluorescence compared to non-treated controls. A similar induction is caused by addition of the iron chelator EDDA (1 mM), suggesting that bacteria exposed to the metallo-complex "sense" iron limiting conditions. Addition of gallium (1 mM) alone resulted in a two-fold reduction in fluorescence, similar to the effect observed with the addition of iron, indicating that addition of gallium mimics an iron-rich environment.

Not wanting to be limited by the theory, these results suggest a possible explanation for the higher anti-microbial efficacy of gallium-desferrioxamine as compared to gallium-alone: the iron replete response triggered by gallium alone causes the cells to reduce activity of iron uptake mechanisms, which are also required for gallium intake. This will result in reduced gallium accumulation that may help protect the cells from its toxic effect. In contrast, when gallium-desferrioxamine is added, all the free iron outside the cells is chelated by the desferrioxamine component. This will result in uptake and accumulation within bacteria of both gallium and particularly gallium-desferrioxamine, which is in excess. Once internalized, the gallium-desferrioxamine complex (unlike the Fe(III)-desferrioxamine complex) remains intact, does not decompose, and cause the toxic response. In addition, this triggers an iron starvation response and sets off a "vicious cycle," by which attempts of the cell to further augment iron uptake result in even greater accumulation of gallium-desferrioxamine and gallium, thus promoting additional uptake and intensifying the toxic effects.

Example 5

Effects of Gallium-Desferrioxamine on *Staphylococcus aureus* (MRSA Strain) and *Escherichia coli*

The effect of gallium-desferrioxamine against the drug resistant bacterial was investigated. The efficacy of DFO-Ga against common biofilm pathogens *Staphylococcus aureus* (MRSA strain) and *Escherichia coli* was examined. Biofilms were grown using the spinning disc reactor system as above. Spinning disc reactor biofilms with *E. coli* or MRSA *S. aureus* were treated for 24 h. The concentration of DFO-Ga in both treatments was (1 mM). In the *E. coli* treatment, the concentration of Gm was 10 µg/ml and for the combination of DFO-Ga (1 mM) and Gm (10 µg/ml).

Figure 12A:
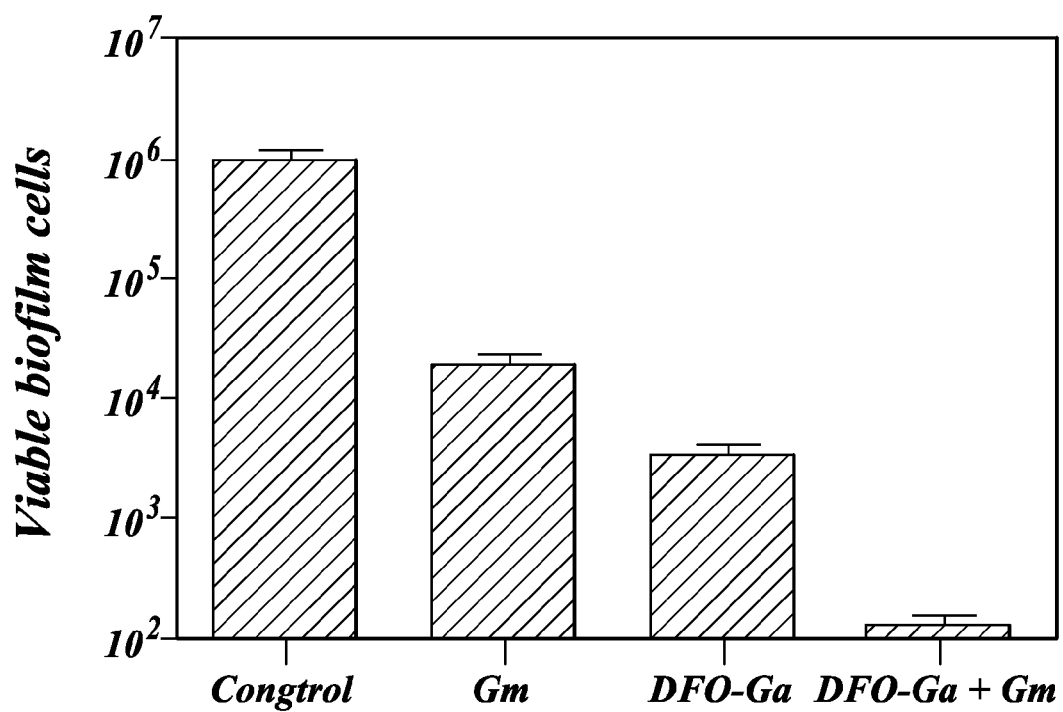
FIG. 12A compares the activity of gentamicin, gallium-desferrioxamine, and the combination of gallium-desferrioxamine and gentamicin against *E. coli*.
Figure 12B:
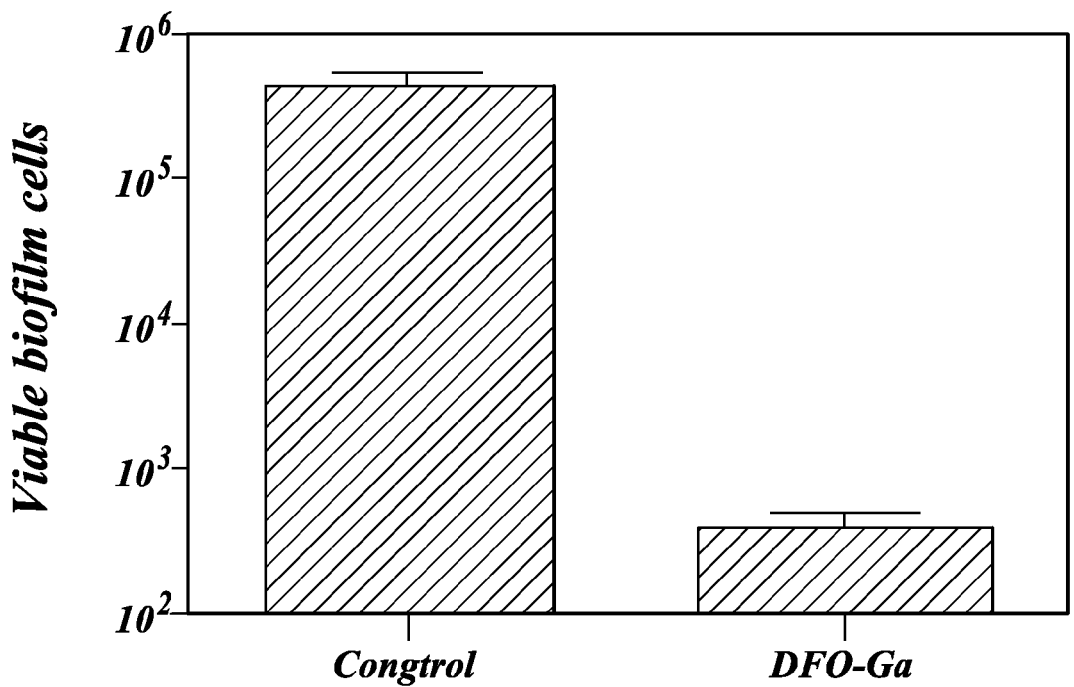
FIG. 12B shows that gallium-desferrioxamine is effective against methicillin resistant *S. aureus* biofilms cells.

As shown in FIG. 12A, the combination of DFO-Ga with Gm caused a 4 log reduction on viable *E. coli* biofilm bacteria. As shown FIG. 12B, DFO-Ga was able to reduce the viable *Staphylococcus aureus* biofilm bacteria by approximately 3 log units. These results prove the ability of gallium-desferrioxamine to serve as a broad spectrum antibacterial and anti-biofilm agent against bacterial pathogens, in general, both Gram negative and Gram positive.

Example 6

Treatment of Rabbit Cornea Infections with a Representative Metallo-Desferrioxamine Complex New Zealand Albino rabbits weighing 2.5-3.5 kg were used. For induction of keratitis, animals were anesthetized with ketamine HCl (50 mg/kg, Ketaset, Fort Dodge Animal Health, Fort Dodge, Iowa) injected intramuscularly in combination with the relaxing agent xylazine (5.0 mg/kg, XYL-M2, Veterinary, VMD, Arendonk, Belgium). Local anesthetic drops (Benoxinate HCl 0.4%, Fisher Pharmaceuticals, Tel-Aviv, Israel) were topically applied to the cornea prior to scarification and contact lens application. At this time, the horizontal diameter in the middle of the cornea (limbus-to-limbus) was measured using calipers; this was later used as a reference to measure areas of infiltrate and epithelial erosion from photographs. A 2 mm long and 160 µm deep cut was made in the center of the cornea by using a diamond keratome (45' Micrometer Diamond Keratome, HUCO, Switzerland). After the incision was made a contaminated lens (prepared as described below) was applied to the ocular surface, and the eyelid was sutured shut. The sutures were released after 10 h, the contact lens removed, and the animals were followed until the corneal infiltrate and erosion reached the threshold size for treatment initiation. This was defined as an infiltrate with an area of 3.6-4 mm and an epithelial erosion with an area of 8.0-8.4 mm in at least one axis of the lesion. This occurred in most cases between 1-4 h after removal of the contact lens. Bacteria used to initiate the infection were grown overnight at 37° C. in Tryptic Soy Broth with shaking, sub-cultured in fresh TSB, and grown to the late logarithmic phase ($10^9$ cells per ml). Sterile soft contact lenses (Platinum Everyday Super, St. Shine, Taiwan) were suspended in the bacterial culture for 2 h at 37° C. and then inserted into the eye. At the end of the experiment, animals were euthanized with Pentobarbitone (Pental veterinary, CTS Chemical Industries Ltd, Tel-Aviv, Israel) and eyes were enucleated for histological processing and evaluation.

Infected eyes were randomly assigned to one of 5 topical treatment groups; a control group was sham treated with ophthalmic artificial tears (Hadassah Medical Center Pharmacy, Jerusalem, Israel), which also served as the vehicle for the other treatment groups. The four other groups all received artificial tears eye drops containing 0.5% gentamicin, either alone or in combination with 3.5 mM gallium-desferrioxamine, 3.5 mM desferrioxamine or 3.5 mM $GaCl_3$. Treatment was initiated once the infected corneal lesion reached the threshold size detailed above, and a regimen closely resembling that used in the human clinical setting was applied: drops were administered q15 min for the first 4 h, q30 min between 4-12 h, q1 h between 12-48 h, and between 48-96 h q2 h during the day (12 h) with tobramycin 0.3% ointment (Tobrex: Alcon Couvreur N.V. Puurs, Belgium) applied overnight. Treatment ceased at 96 h, but animals were followed until sacrificed at different intervals up to 14 days following treatment initiation.

To document the clinical progression of the infectious process, serial digital color photographs were taken: conventional color photographs were used to monitor the corneal infiltrate, degree of diffuse corneal opacity and scarring, level of hypopyon in the anterior chamber of the eye and extent of iris injection as described previously. Photographs following application of fluorescein to the cornea were used to measure the area of corneal epithelial erosion. Initial photographs were taken immediately following removal of the sutures and contact lens, and then again upon initiation of treatment. From this point on conventional color photos were taken q2 h between 0-12 h, q4 h between 12-24 h, q6 h between 24-96 h and q24 h between 96 h and the time of sacrifice. Photographs of fluorescein staining were taken q4 h between 0-24 h, and from then on at the same time intervals in which regular color photos were taken. Grading of the area of corneal infiltrate and scarring, the area of corneal epithelial erosion, and the degree of corneal opacity (outside of the main infiltrate), were as described previously. The area of corneal infiltrate, scarring and erosion were measure from digitized photographs. For statistical analyses we used SPSS 7.1 (SPSS Inc., Chicago, Ill.). The statistical significance between the different treatment groups was determined using the Kruskal-Wallis and Mann-Whitney tests.

Figure 13A:
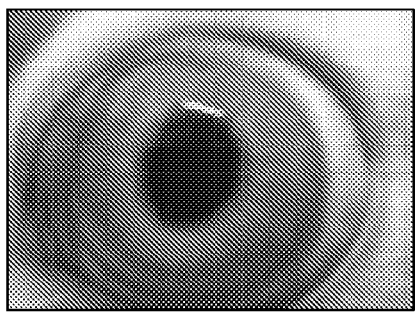
FIG. 13A is the image normal uninfected eye.
Figure 13B:
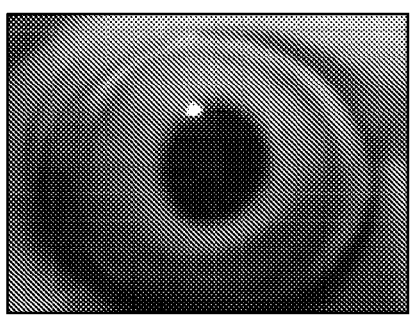
FIG. 13B is the image of fluorescein-stained normal uninfected eye.
Figure 13C:
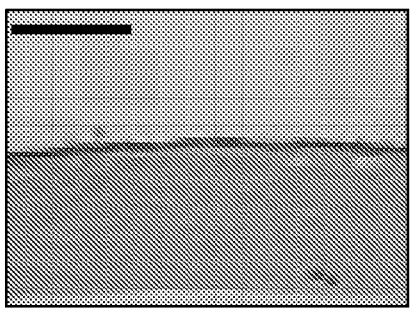
FIG. 13C shows the histopathology in normal uninfected cornea.

FIG. 13 shows representative images of a normal uninfected rabbit cornea. FIGS. 14-18 compare the images of infected rabbit cornea after treating with different reagents. Top photographs show the extent of infection and infiltrate. Middle photographs of fluorescein-stained eyes show the extent of epithelial injury. Bottom images show histopathology in corneas from different experimental groups.

Figure 14A:
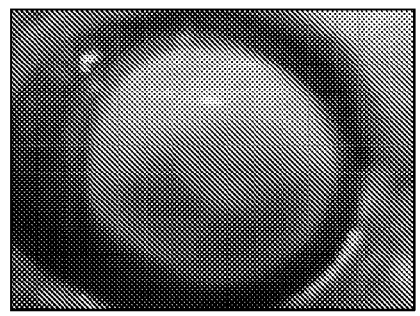
FIG. 14A is the image of the infected eye.
Figure 14B:
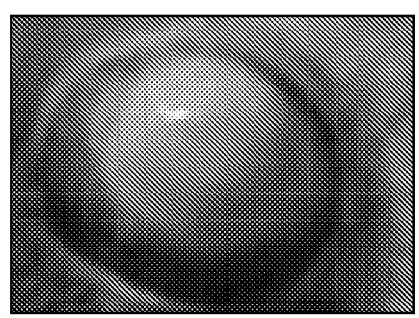
FIG. 14B is the image of fluorescein-stained infected eye.
Figure 14C:
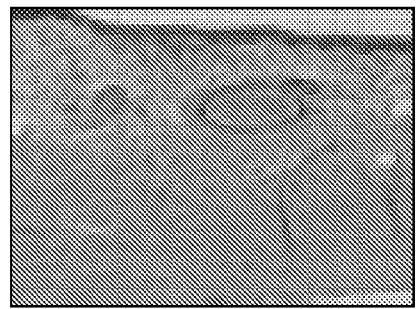
FIG. 14C shows the histopathology in the infected cornea.
Figure 15A:
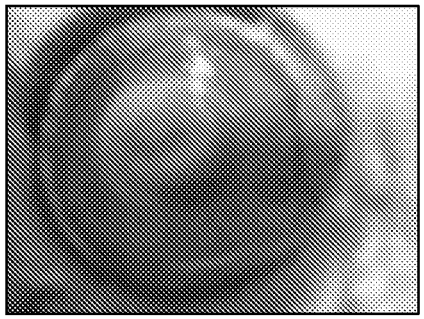
FIG. 15A is the image of the infected and treated eye.
Figure 16A:
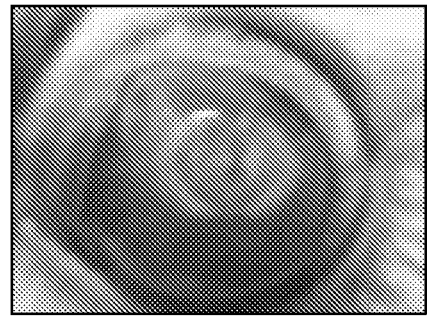
FIG. 16A is the image of the infected and treated eye.
Figure 15B:
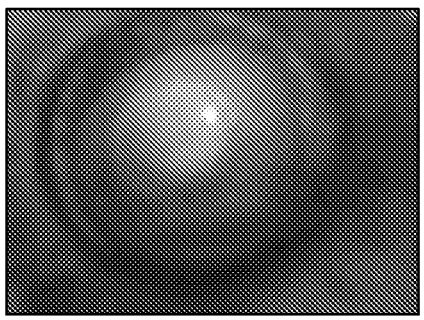
FIG. 15B is the image of fluorescein-stained infected and treated eye.
Figure 16B:
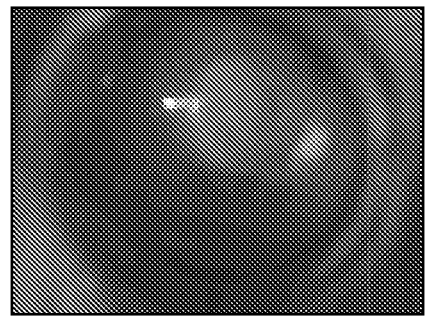
FIG. 16B is the image of fluorescein-stained infected and treated eye.
Figure 15C:
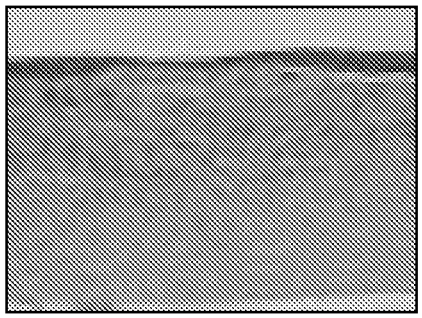
FIG. 15C shows the histopathology in the infected and treated cornea.
Figure 16C:
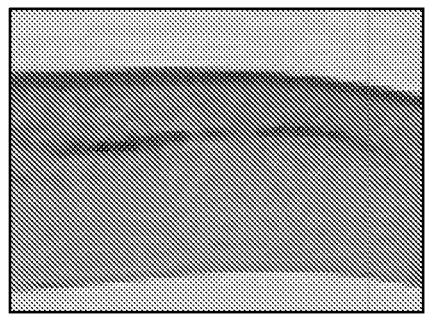
FIG. 16C shows the histopathology in the infected and treated cornea.
Figure 17A:
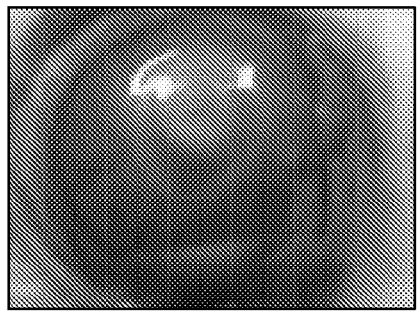
FIG. 17A is the image of the infected and treated eye.
Figure 18A:
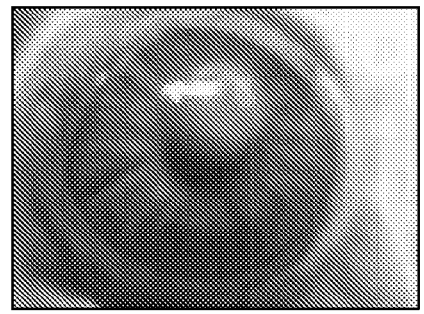
FIG. 18A is the image of the infected and treated eye.
Figure 17B:
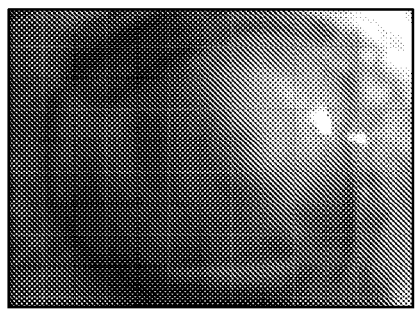
FIG. 17B is the image of fluorescein-stained infected and treated eye.
Figure 18B:
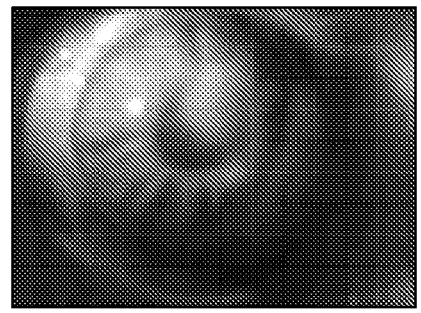
FIG. 18B is the image of fluorescein-stained infected and treated eye.
Figure 17C:
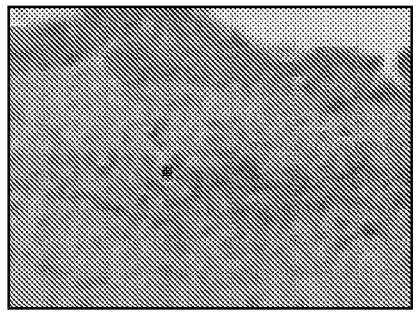
FIG. 17C shows the histopathology in the infected and treated cornea.
Figure 18C:
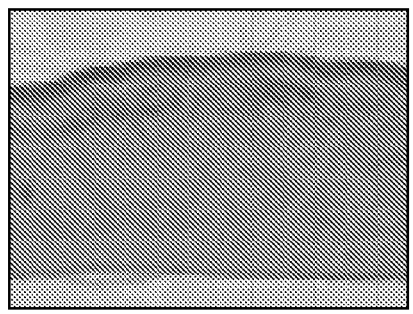
FIG. 18C shows the histopathology in the infected and treated cornea.

As shown in FIG. 15, the infection is resolved within 120 h with gentamicin treatment, but significant scarring persists. As shown in FIG. 14, with a sham treatment (artificial tears in place of gentamicin), the infection spreads rapidly and there is complete corneal opacification that is often accompanied by intra-ocular penetration of the infection within 48-96 h. As shown in FIG. 18, when a combination of gallium-desferrioxamine and gentamicin is used, the corneal infiltrate, extent of epithelial erosion, and ultimate scar area are reduced by approximately 50% as compared to gentamicin alone. Treatments with gentamicin plus desferrioxamine (FIG. 16) or plus gallium (FIG. 17) are not significantly different than treatment with gentamicin alone (FIG. 15).

Figure 19:
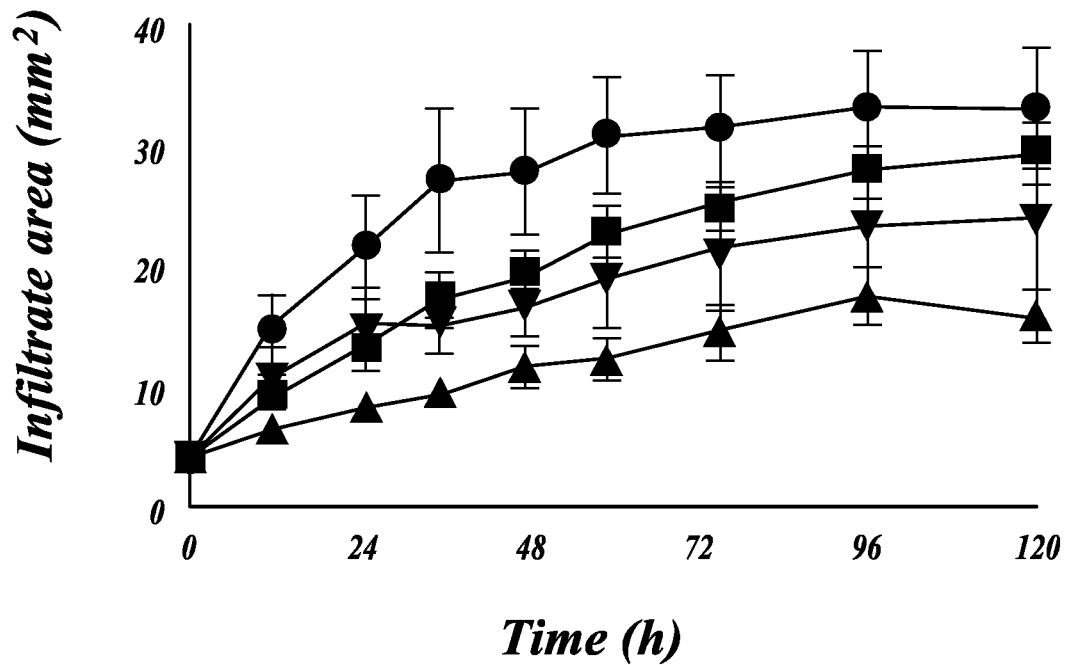
FIG. 19 graphically compares the extent of corneal infiltrate in rabbit corneas infected with *P. aeruginosa* and treated with Gm (squares), Gm+Ga (circles), Gm+DFO (upside-down triangles), and the combination of gallium-desferrioxamine and gentamicin (right-side up triangles) over time, demonstrating that eyes treated with gentamicin plus gallium-desferrioxamine fared better than eyes treated with gentamicin alone at all time points.

FIG. 19 compares the extent of corneal infiltrate in rabbit corneas infected with *P. aeruginosa* and treated with gentamicin, gentamicin and gallium, gentamicin and desferrioxamine, and gentamicin and gallium-desferrioxamine over time. FIG. 19 demonstrates that eyes treated with the combination of gentamicin and gallium-desferrioxamine fared better than eyes treated with gentamicin alone at all time points ($p<0.05$). The other treatment groups showed responses that were not significantly different from Gm alone.

Figure 20:
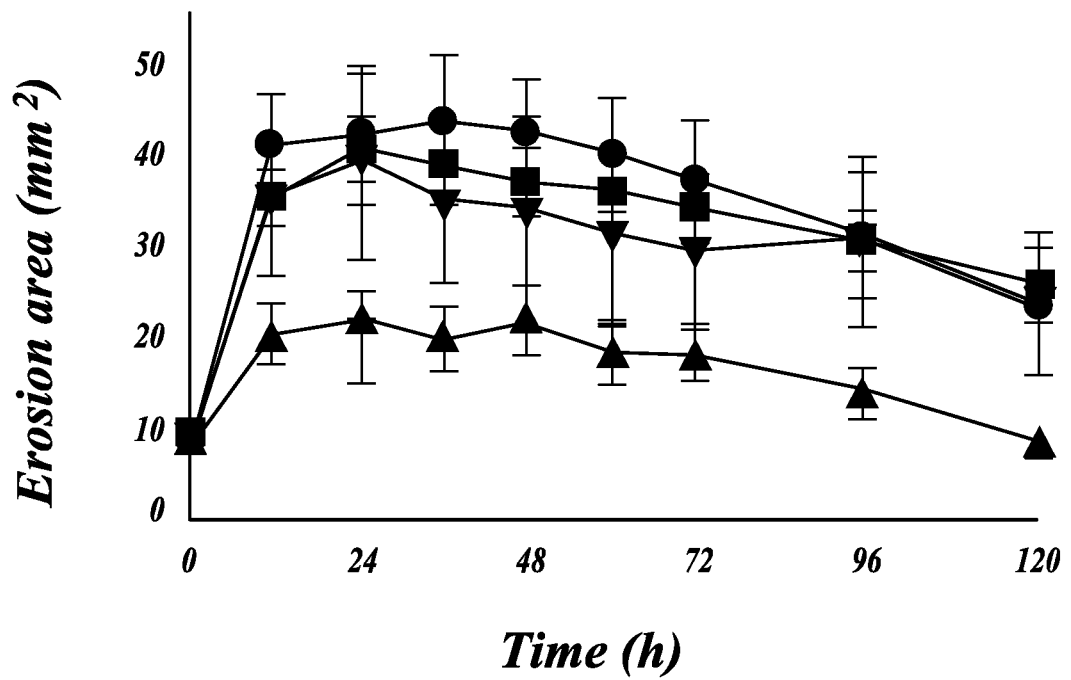
FIG. 20 graphically illustrates the epithelial corneal erosion in rabbit corneas infected with *P. aeruginosa* and treated with gentamicin (squares), the combination of gentamicin and gallium (circles), the combination of gentamicin and desferrioxamine (upside-down triangles), and the combination of gentamicin and gallium-desferrioxamine (right-side up triangles) over time, demonstrating that eyes treated with the combination of gentamicin and gallium-desferrioxamine fared better than eyes treated with gentamicin alone at all time points.

FIG. 20 compares the epithelial corneal erosion in rabbit corneas infected with *P. aeruginosa* and treated with gentamicin, gentamicin and gallium, gentamicin and desferrioxamine, and gentamicin and gallium-desferrioxamine over time. FIG. 20 demonstrates that eyes treated with the combination of gentamicin and gallium-desferrioxamine fared better than eyes treated with gentamicin alone at all time points.

These results indicate that addition of gallium-desferrioxamine to the gentamicin treatment results in a less aggressive infection and allows for faster healing. Additional parameters of disease severity such as corneal opacity, iris injection, and degree of hypopion are also improved following addition of topical gallium-desferrioxamine to the gentamicin treatment.

While illustrative embodiments have been illustrated and described, it will be appreciated that various changes can be made therein without departing from the spirit and scope of the invention.

The invention claimed is:

1. A method for treating a human or animal subject in need of such treatment, comprising administering to the subject an amount of a metallo-desferrioxamine complex effective to inhibit bacterial infection in the subject, wherein the metallo-desferrioxamine complex comprises a metal ion selected from the group consisting of gallium and zinc.

2. The method of claim 1, wherein the metallo-desferrioxamine complex is gallium-desferrioxamine.

3. The method of claim 1, wherein the metallo-desferrioxamine complex is zinc-desferrioxamine.

4. The method of claim 1, wherein the effective amount is from about 1.0 to about 30 mg/kg body weight.

5. The method of claim 1, wherein the metallo-desferrioxamine complex is administered in a pharmaceutically acceptable carrier.

6. The method of claim 1, wherein the bacterial infection an infection by a bacteria selected from the group consisting of *Staphylococcus aureus*, *Staphylococcus epidermidis*, *Escherichia coli*, *Klebsiella pneumoniae*, *Proteus mirabilis*, *Alcaligenes faecalis*, and *Neisseria meneningitidis*, and species of *Salmonella*, *Enterobacter Pseudomonas*, and *Providencia*.

7. The method of claim 1, wherein the bacterial infection is a *Pseudomonas aeruginosa* infection.

8. The method of claim 1, wherein the bacterial infection is an infection of the eyes, lungs, gut, or oral cavity.

9. The method of claim 1, wherein the bacterial infection is an acute ulcerative corneal infection.

10. The method of claim 1, wherein the bacterial infection is a chronic biofilm-associated lung infection.

11. The method of claim 1, wherein the metallo-desferrioxamine complex is administered in combination with an antibacterial agent.

12. The method of claim 11, wherein the antibacterial agent is selected from the group consisting of aminoglycosides, penicillins, cephalosporins, macrolides, fluoroquinolones, sulfonamides, tetracyclines, and doxycyclines.

13. The method of claim 11, wherein the antibacterial agent is selected from the group consisting of gentamicin, tobramycin, amoxicillin, cephalexin, erythromycin, clarithromycin, azithromycin, ciprofloxacin, levofloxacin, ofloxacin, co-trimoxazole, trimethoprim, sumycin, panmycin, and vibramycin.

14. The method of claim 11, wherein the metallo-desferrioxamine complex is gallium-desferrioxamine and the antibacterial agent is gentamicin.

15. The method of claim 1, wherein the metallo-desferrioxamine complex is administered by ophthalmic, inhalation, topical, dental, vaginal, oral, parenteral, or systemic methods.

16. A method of inhibiting bacterial growth comprising contacting bacteria with an amount of a metallo-desferrioxamine complex effective to inhibit growth of the bacteria, wherein the metallo-desferrioxamine complex comprises a metal ion selected from the group consisting of gallium and zinc.

17. The method of claim 16, wherein the metallo-desferrioxamine complex is administered in combination with an antibacterial agent.

18. The method of claim 17, wherein the antibacterial agent is selected from the group consisting of aminoglycosides, penicillins, cephalosporins, macrolides, fluoroquinolones, sulfonamides, tetracyclines, and doxycyclines.

19. The method of claim 16, wherein the metallo-desferrioxamine complex is administered by ophthalmic, inhalation, topical, dental, vaginal, oral, parenteral, or systemic methods.

20. A method for treating a human or animal subject in need of such treatment, comprising administering to the subject an amount of a metallo-desferrioxamine complex effective to inhibit bacterial infection in the subject, wherein the metallo-desferroxamine complex comprises a metal ion selected from the group consisting of gallium and zinc, and the bacterial infection is a *Staphylococcus aureus, Staphylococcus epidermidis, Escherichia coli, Klebsiella pneumoniae, Proteus mirabilis, Alcaligenes faecolis*, and *Neisseria meningitidis*, and species of *Salmonella, Enterobacter, Pseudomonas*, or *Providencia* infection.

21. The method of claim 20, wherein the bacterial infection is a *Pseudomonas aeruginosa, Staphylococcus aureus*, or *Escherichia coli* infection.

* * * * *

UNITED STATES PATENT AND TRADEMARK OFFICE
CERTIFICATE OF CORRECTION

PATENT NO. : 8,680,148 B2
APPLICATION NO. : 11/838177
DATED : March 25, 2014
INVENTOR(S) : E. P. Greenberg et al.

Page 1 of 1

It is certified that error appears in the above-identified patent and that said Letters Patent is hereby corrected as shown below:

In the Claims

| COLUMN | LINE | ERROR |
|---|---|---|
| 18 (Claim 6, | 43 line 1) | "infection an" should read --infection is an-- |
| 18 (Claim 6, | 47 line 5) | "meneningitidis" should read --meningitidis-- |

Signed and Sealed this
First Day of December, 2015

Michelle K. Lee
*Director of the United States Patent and Trademark Office*